United States Patent [19]

Markowitz et al.

[11] Patent Number: 4,951,667
[45] Date of Patent: Aug. 28, 1990

[54] DUAL CHAMBER ACTIVITY RESPONSIVE PACER

[75] Inventors: H. Toby Markowitz, Roseville; Kevin Prest-Berg, Stillwater; David L. Thompson, Fridley, all of Minn.

[73] Assignee: Medtronic, Inc., Minneapolis, Minn.

[21] Appl. No.: 450,958

[22] Filed: Dec. 12, 1989

Related U.S. Application Data

[63] Continuation of Ser. No. 125,422, Nov. 25, 1987, Pat. No. 4,890,617.

[51] Int. Cl.⁵ ............................................. A61N 1/00
[52] U.S. Cl. ............................................. 128/419 PG
[58] Field of Search ........ 128/419 PG, 419 P, 419 PS

[56] References Cited

U.S. PATENT DOCUMENTS 4,781,194 11/1988 Elmquist ..................... 128/419 PG
4,856,521 8/1989 Irnich ............................ 128/419 PG

*Primary Examiner*—Francis Jaworski
*Assistant Examiner*—George Manuel
*Attorney, Agent, or Firm*—Joseph F. Breimayer; Reed A. Duthler

[57] ABSTRACT

An activity responsive, rate adaptive pacer, which senses and paces in both the atrium and ventricle is disclosed. The pacing rate displayed by the pacer is determined by the sensed activity of the patient, the programmed lower rate, and the patient's atrial or sinus rate.

3 Claims, 9 Drawing Sheets

DUAL CHAMBER ACTIVITY RESPONSIVE PACER

This is a continuation of copending application Ser. No. 125,422, filed Nov. 25, 1987, now U.S. Pat. No. 4,890,617.

BACKGROUND OF THE INVENTION

1. Field of the Invention

The invention relates to cardiac pacemakers, and more particularly to a dual chamber rate responsive pacemaker which alters the pacemaker's V-A escape interval in response to the exercise level of the patient.

2. Description of the Prior Art

Various types of pacemakers are disclosed in the prior art.

The first pacemakers were asynchronous (VOO), and they stimulated the heart at a fixed rate, independent of the patient's underlying cardiac rhythm. Although such pacers, typified by U.S. Pat. No. 3,057,356 to Greatbatch, provide a ventricular pacing rate sufficient to sustain life, this pacing mode can compete with native ventricular rhythms which is undesirable.

Subsequently, demand pacemakers (VVI) were developed. This type of pacer interacts with the patient's heart to provide stimulating pulses only if spontaneous cardiac activity does not occur. An example of such a pacer is taught by U.S. Pat. No. 3,478,746 to Greatbatch. This form of pacer provides a ventricular sense amplifier for detecting ventricular depolarizations. A ventricular sense event resynchronizes the pacer's V-V timer by resetting and restarting it. The ventricular sense event also cancels or inhibits the scheduled ventricular stimulus and thus avoids competition with the native ventricular rhythm.

Also, at this time, atrial synchronized pacers (VAT) were developed. This type of pacer paces the ventricle in response to the detected atrial rate of the patient. The VAT pacer, as typified by U.S. Pat. No. 3,253,596 to Keller, provides an atrial sense amplifier for detecting atrial depolarizations. An atrial sense event starts the pacer's A-V delay timer. When the A-V timer times out, a ventricular stimulus is provided. Conceptually, such a pacer can be considered as a prosthetic conduction pathway which mimics the natural A-V conduction pathways of the heart. One drawback to this form of pacing is its ability to compete with ectopic ventricular activity. An ectopic ventricular beat (PVC) may be detected in the atrium which will result in the generation of a ventricular stimulus a short time after the ventricular depolarization. Although such a pacing regime is considered harmless if the A-V delay is short, it is possible to deliver the pacing stimulus into the vulnerable period of the ventricle and thereby initiate a lethal arrhythmia.

Continued development of pacemakers was marked by the invention of the A-V sequential pacer (DVI), as disclosed in U.S. Pat. No. 3,595,242 issued to Berkovits. This form of pacer provides for stimulation in both the atria and the ventricles while providing sensing in the ventricle. In this DVI mode pacer, a ventricular sense event starts both a V-A and a V-V timer. At the expiration of the V-A escape interval, the pacer delivers an atrial stimulus, and at the end of the V-V escape interval, the pacer delivers a ventricular stimulus. If a ventricular sense event occurs during the V-A or V-V time intervals, the pacer will resynchronize to the ventricular sense event and inhibit the delivery of the otherwise scheduled ventricular stimulus.

The DDI mode pacer described by U.S. Pat. No. 3,747,604 to Berkovits further includes an atrial sense amplifier to inhibit the atrial stimulus if an atrial sense event occurs during the V-A interval. The atrial sense event does not resynchronize the pacer which makes this device espcially suitable in patients where atrial competition must be avoided.

The atrial synchronized ventricular inhibited or VDD mode pacer, as disclosed in U.S. Pat. No. 3,648,707 issued to Greatbatch has structures for sensing in the atrium and ventricle but provides stimulating pulses only in the ventricle. In operation, the VDD pacer will synchronize on detected atrial activity and provide a ventricular stimulus if one does not occur within the A-V delay initiated by the atrial depolarization. Ventricular sense events both inhibit the delivery of the otherwise scheduled stimulus and also resynchronize the pacer's V-V timer.

More recently, the dual sense-dual pace DDD mode pacers, as first described by U.S. Pat. No. 4,312,355 to Funke, have been introduced. The DDD pacer addresses many of the shortcomings of the prior art devices.

The DDD mode pacer, as described by Funke, has had wide application. This type of pacer has sense amplifiers for detecting both atrial and ventricular events, as well as output pulse circuits for stimulating both the atrium and the ventricle. This form of prior art pacer provides timing circuitry to initiate an A-V delay upon the occurrence of an atrial event. If, during the A-V delay period, no spontaneous ventricular event is sensed, the pacer will produce a ventricular stimulus at the conclusion of the A-V delay period. Similarly, upon the occurrence of a ventricular event, the timing circuitry initiates a V-A delay period. If, during the V-A interval, no spontaneous atrial event is sensed, the pacer will produce an atrial stimulus at the conclusion of the V-A interval.

In this type of pacer, both the programmed A-V and V-A intervals are fixed, and in the absence of spontaneous P-waves or R-waves, the pacer will pace the heart at fixed A-A and R-R intervals. However, if the ventricle depolarizes spontaneously, then the A-V is truncated and the observed A-A interval is not fixed and will be shorter than the arithmetic sum of the programmed A-V and V-A intervals.

In contrast to this behavior, other forms of DDD pacing have been proposed and built. One such pacemaker which is important to the understanding of the present invention is described in U.S. Pat. No. 4,523,593 to J. C. Rueter. This pacer does not truncate the A-V delay period upon the occurrence of a ventricular sense event and the resultant pacer exhibits constant A-A paced intervals.

The dual chamber modalities, DVI, VAT, VDD and DDD, have proven to be especially efficacious pacemakers since they restore A-V synchrony and thus improve cardiac output by accommodating the hemodynamic contribution of the atrial chambers within the pacing regime. The latter three modes also synchronize the pacing rate to the patient's native atrial or sinus rate and thus provide an increased pacing rate in response to bodily activity. This rate responsive behavior is especially helpful for increasing cardiac output.

More recently, other pacers which increase cardiac output in response to exercise have been proposed.

These include pacemakers which rely upon the sensing of a historical average of atrial activity, blood pH, respiratory rate or QT interval data to alter the pacemaker's escape interval. A discussion of these prior art proposals may be found in "The Exercise Responsive Cardiac Pacemaker", *IEEE Transactions on Biomedical Engineering*, Vol. 12, December 1984.

One approach which is important to the understanding of the present invention is the activity responsive pacer described in U.S. Pat. No. 4,428,378, issued to Anderson et al. The pacer disclosed in U.S. Pat. No. 4,428,378 monitors the physical activity of the patient and increases the pacing rate in response to increasing patient activity.

More recently, integration of activity sensing and dual chamber pacing has been proposed. See "Rate Responsive Dual Chamber Pacing" in *PACE*, Vol. 9, pp. 987-991.

SUMMARY OF THE INVENTION

The description of the pacer of the present invention starts with three hypothetical examples, which illustrate the clinical aspects of the pacer. Next, the timers which perform the major timing operations of the pacer are introduced and described. Next the pacer's functional logic characteristics are described in terms of pacer outputs and inputs. And finally, the function and operation of each of the timers is described individually to complete the description of the invention.

By way of contrast, the present invention incorporates and uniquely integrates an activity sensing system into a dual chamber DDD pacemaker. The pacemaker responds to both the physical activity of the patient as well as the atrial and ventricular depolarizations of the patient.

The pacer is intended for the treatment of patients with bradycardia. In such patients, the sinus rate may be slow or normal and may include ectopic beats. Also, the patient's activity level may vary from rest to active. To accommodate these various conditions, the pacer of the present invention follows the faster of the atrial rate, or the activity sensor based rate, on a beat by beat basis as discussed below.

The pacer exhibits an A-V timing interval which is constant after programming, while the V-A timing interval of the pacer may vary. The basic variations in the observed V-A interval results from one of three mechanisms which may be understood in connection with the following three hypothetical examples.

For the first hypothetical example, assume that the patient is at rest and has both a very slow sinus rate and a very low activity level. In this instance, the observed V-A interval will most likely end with an atrial pace event at a rate which reflects the lower rate setting selected by the physician during the programming of the pacer.

For the second hypothetical example, assume that the patient is sedentary but has normal sinus rate. In this instance, naturally occurring P-waves will be sensed by the pacer and truncate the V-A interval with an atrial sense event. In this case, the atrial channel of the pacer will be inhibited and may lead to a V pace event.

For the third hypothetical example, assume that the patient is quite active but has a very low sinus rate. In this instance, the V-A interval would typically end with an atrial pace event at a rate which reflects the activity level of the patient.

Conceptually the preferred pacer for carrying out the present invention may be considered as comprising three separate timers. Two timers are devoted to timing out the pacer's V-A interval. The first V-A timer (LRT) sets an escape interval corresponding to the programmed lower rate of the pacer as in the Funke pacer. The second V-A timer (PAB+ACT) sets a variable escape interal which depends on the patient's activity level as in the Anderson and Brumwell pacer. Both of these timers are started at the same time, however. Whichever one of the two timers times out first provokes an atrial pace event. While these two pacer timers race to pace the atrium, a third physiologic timer located in the S-A node of the heart is likewise in the race. This natural pacemaker may initiate a natural atrial contraction at approximately the same time as the second V-A timer under some circumstances which may lead to atrial competition.

The present pacemaker resolves the potential conflict between natural and artificial stimulation described above as follows. If the heart beats first, then the pacer will detect this and generate an atrial sense event within the relative refractory portion of the post ventricular atrial refractory period (PVARP). This atrial sense event will inhibit the atrial pace signal generated by the second V-A timer (PAB+LRT). In essence, atrial sensing early in the V-A period will cancel the activity based atrial pacing signal. Turning to the effect of this atrial sense event on the first timer, we find conventional behavior as displayed by prior art DDD pacers. The atrial sense event in the PVARP is "ignored" by the pacer which results in an atrial pace event coincidental with the time out of the LRTVATO. Thus if the heart beats first, the pacer defers to the natural pacemaker and won't pace in the atrium on an activity basis for that cardiac cycle.

The third A-V timer is devoted to timing out the pacer's A-V delay period. This timer is started by atrial events which is conventional as in the Funke pacer. However, unlike the Funke pacer, ventricular sense events which occur during this A-V interval do not resynchronize the pacer to the R-wave because the A-V timer is not reset or restarted. The ventricular sense event does, however, inhibit the ventricular pace event which would otherwise occur.

Providing each of these pacemaker responses in the presence of ectopic beats, muscle noise, bradycardia and tachycardia requires that the pacer address a myriad of technical problems which will be addressed in the detailed description of the structure and function of the pacer.

To facilitate the description, a drawing is provided which depicts the timing intervals of the pacer timers and which illustrates how these intervals relate to the stimulated surface ECG of the patient.

DETAILED DESCRIPTION OF THE INVENTION

Figure 1:
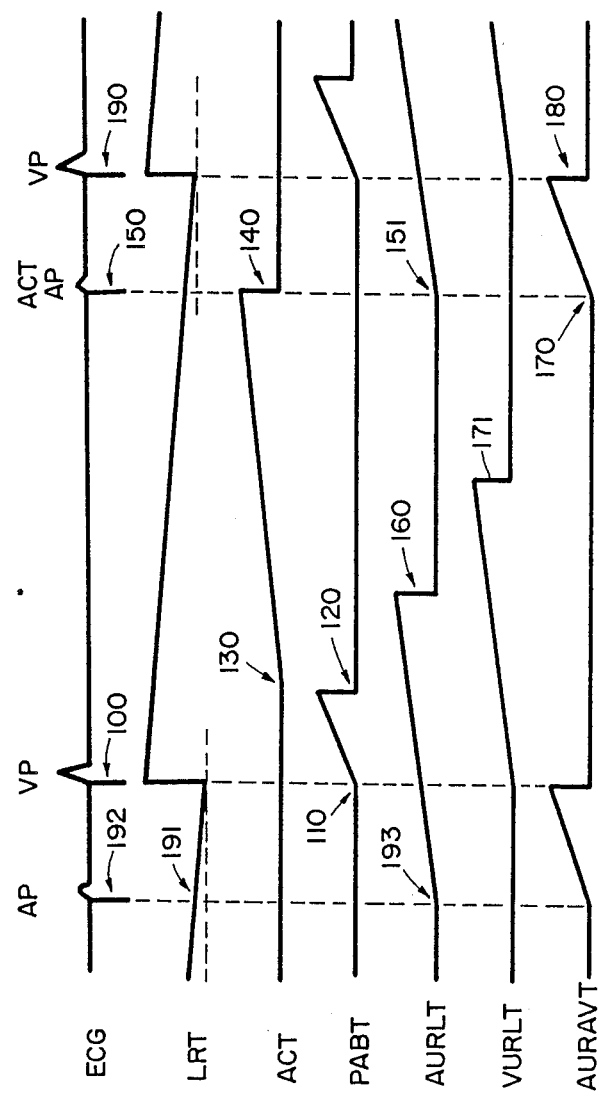
FIG. 1 is a timing diagram depicting activity based pacing in the atrium.

The structure of the present invention includes a force sensor located within the pacemaker as well as signal conditioning circuits which generate a signal indicative of the physical activity level of the patient. Activity monitoring circuitry suitable for implementing the invention is disclosed in Anderson et al U.S. Pat. No. 4,428,378 issued on Jan. 31, 1984, which is incorporated by reference.

Structure

Modern pacers typically include a number of timers which are started and stopped by events sensed by the pacer. For example, a prior art Symbios® pacer may sense atrial and ventricular events occurring within the heart and conform its stimulation regime to the DDD mode. The present invention is based upon the prior art DDD Symbios® pacer which includes a number of timers which are important in understanding the invention and which are summarized viz:

LRT is the lower rate timer.
VURLT is the ventricular upper rate limit timer.
AURAVT is the atrial upper rate A-V delay timer.
AURLT is the atrial upper rate limit timer.

In addition to these timers, the present invention further includes the following timers not found in prior AV+DDD pacers, viz:

PABT is the activity blanking timer.
ACT is the activity modulated timer.

To understand the function of the enumerated timers, reference may be made to the following definitions:

VS is a ventricular sense event outside of ventricular refractory.
VP is a ventricular pace event.
PVC is the second of two consecutive ventricular events with no intervening atrial event.
AS is an atrial sense event outside the atrial refractory period.
AP is an atrial pace event.
AURS is an atrial sense event occurring during the atrial upper rate limit period.
ARS is an atrial sense event occurring within the atrial refractory period.
AURLTO is the time out of the atrial upper rate limit timer. This event permits an atrial pace event.
LRTVATO is the time out of the lower rate based V-A escape interval timer. This event may generate an atrial pace signal.
LRTAVTO is the time out of the lower rate based A-V delay timer. This event may generate a ventricular pace signal.
ACTTO is the time out of the activity modulated V-A escape interval timer. This event may generate an atrial pace signal.
VSPAVTO is the time out of the ventricular safety pace A-V delay timer which occurs when a VS occurs within 110 ms of an AP. This signal is decoded from the AURLT timer. This event may generate a ventricular pace signal.
AURAVTO is the time out of the atrial upper rate A-V delay timer. This event may generate a ventricular pace signal.
VURLTO is the time out of the ventricular upper rate limit timer. This event permits a ventricular pace event.

As previously described in the hypothetical examples, the pacemaker monitors both the physiologic atrial rate and an activity based rate. The pacer must decide which of the two indicated rates it will follow. The pacemaker elects between the two indicated rates on a beat-to-beat basis, and typically, the higher of the two rates is selected by the pacer through the operation of the enumerated timers. Once the pacer synchronizes its operation at the desired rate, the next issue to be addressed is which chamber of the heart should be paced and under what conditions.

Function

A. Atrial Pace Events

There are two sequences of events which will cause the pacer to issue an atrial stimulus to the heart.

The first sequence which results in an activity based atrial pace event which occurs at the end of an activity based V-A escape interval. This first sequence is shown on FIG. 1. The ventricular pace event (VP) as shown at 100 starts the activity blanking timer (PABT) at 110. This timer is programmable and the duration of its time period is used to tailor the activity response characteristics of the pacer. At the time out of the PABT at 120, another timer (ACT) is started as shown at 130. This activity modulated timer (ACT) has a variable time period which is inversely proportional to the activity of the patient. The time out of this timer (ACTTO) at 140 provokes an atrial pace event (AP) at 150.

This description assumes that no atrial events are sensed ($\overline{AS}$) and that no atrial events occur during relative refractory period ($\overline{ARS}$). Also assumed is that the atrial upper rate limit timer (AURLT) has timed out (AURLTO), as shown at 160 to permit atrial pacing.

In Boolean notation, this first atrial pace sequence, which depicts basic activity pacing, may be expressed viz:

$$AP = ACTTO \cap \overline{ARS} \cap \overline{AS} \cap AURLTO \qquad \text{Expression 1}$$

The second sequence, which results in an atrial pace, generates the AP event at the end of a lower rate based V-A escape interval based upon the programmed lower rate.

This sequence begins with a ventricular event, either sense (VS) or pace (VP) which starts a lower rate timer (LRT). This timer is programmable and is set by the physician to a value reflecting the desired V-A time interval in the absence of sinus rhythm or activity. After the desired V-A time is reached, a decoded time out signal (LRTVATO) shown on FIG. 1 at 191 is generated which provokes an atrial pace event (AP) shown on FIG. 1 at 192.

Once again, it has been assumed that no atrial sense events have occurred and that the atrial upper rate limit timer has timed out (AURLTO).

In Boolean notation, this second atrial pace sequence may be expressed:

$$AP = LRTVATO \cap AURLTO \cap \overline{AS} \cap \overline{ARS} \cap \overline{ACTTO} \quad \text{Expression 2}$$

Both conditions for atrial pacing previously discussed require that the atrial upper rate limit timer (AURLT) time out (AURLTO). The purpose of this conventional timer (AURLT) is to prevent atrial pacing while the timer is operating. Five events can start the AURLT. These are: (ACTTO∩AURLTO); LRTVATO; AS PVC; and a Wenckebach event. Recall that (ACTTO∩AURLTO) and LRTVATO both give rise to atrial pacing. Therefore, one might describe the atrial upper rate timer as starting upon atrial sense events or events which would give rise to an atrial pace event.

B. Ventricular Pace Events

The pacemaker of the present invention paces in the ventricle if no naturally occurring ventricular event occurs in the A-V timing interval of the pacemaker. There are three sequences of events which will cause the pacer to issue a ventricular pacing stimulus.

As in the DDD pacing modality, a ventricular pace event (VP) occurs one A-V interval after an atrial event, either sense (AS) or pace (AP). In the absence of a ventricular sense event ($\overline{VS}$), the pacer's lower rate timer (LRT) will time out a programmed A-V delay. At time out (LRTAVTO), the pacer will generate a ventricular pace VP.

In this example, we assume that there has been no sensed ventricular activity $\overline{VS}$ in the A-V interval, and we assume that the ventricular rate limit timer has timed out VURLTO.

This first sequence giving rise to ventricular pacing may be expressed:

$$VP = VURLTO \cap LRTAVTO \cap \overline{VS} \quad \text{Expression 3}$$

Figure 6:
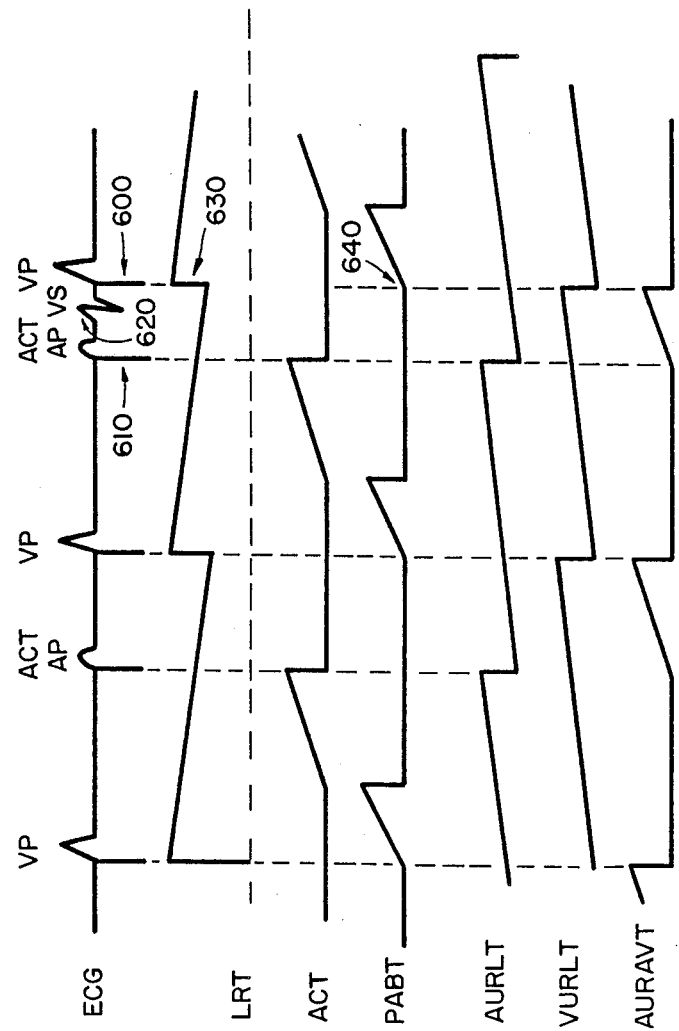
FIG. 6 is a timing diagram depicting ventricular safety pacing.

The second sequence of events which may generate a ventricular pace event is called ventricular safety pace and is illustrated on FIG. 6. This is a programmable feature of prior art pacers which may be programmed off by the physician if desired. However, when integrated with activity pacing, it operates as follows. A ventricular safety pace (VSP) at 600 will occur 110 ms after an atrial pace (AP) at 610 if a ventricular sense event (VS) occurs during this 110 ms time period as shown at 620. This ventricular safety pace time interval is timed out by decoding from the atrial upper rate limit timer. Thus, this VP occurrence may be expressed:

$$VP = VSPAVTO \cap VS \quad \text{Expression 4}$$

The third sequence which may generate a ventricular pace event results from an A-V delay escape interval which is timed by an atrial upper rate AV timer (AURAVT). This may be expressed:

$$VP = AURAVTO \cap \overline{VS} \cap VURLTO \quad \text{Expression 5}$$

There are three events can start the AURAVT. These events are: (ACTTO∩AURLTO); AS; and LRTVATO. Examples of these sequences are shown throughout the figures. On FIG. 1, there is shown an example of how the time out of the activity modulated timer (ACTTO) starts the AURAVT. The time out of ACT shown at 140 starts the atrial upper rate A-V timer (AURAVT) at 170. The ventricular pace event (VP) shown at 190 occurs because of the time out of AURAVT shown at 180. Note that the VURLT had already timed out at 171. This example shows how ACTTO can start the AURAVT.

Figure 2:
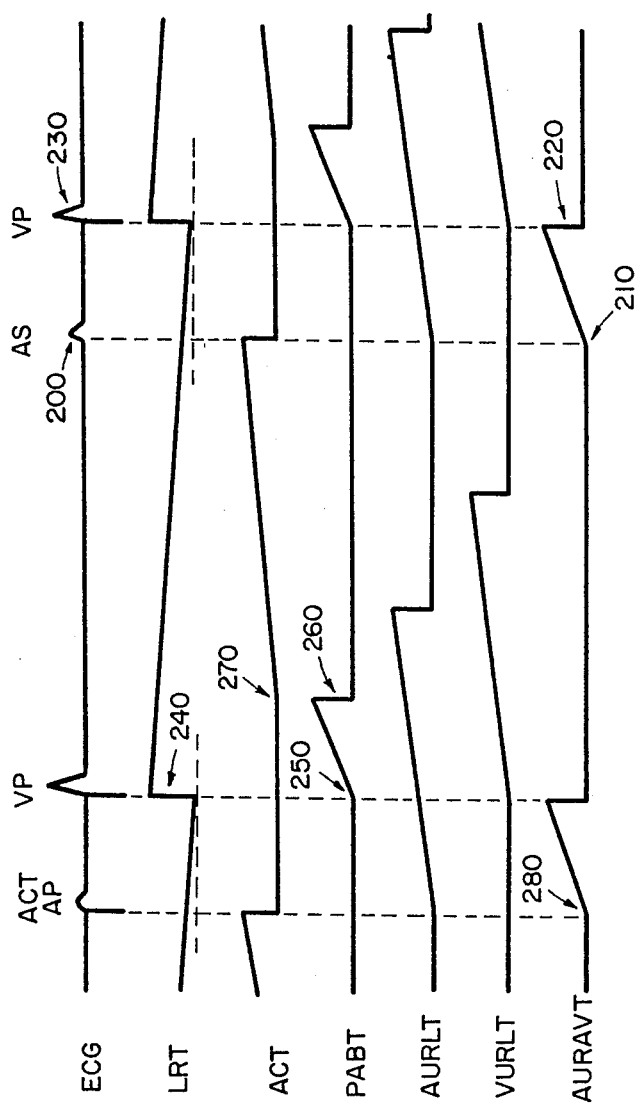
FIG. 2 is a timing diagram depicting pacing where the sinus rate is faster than the activity rate.

An example of AURAVT started by an atrial sense event is shown at FIG. 2 where AS event 200 starts the atrial upper rate A-V timer (AURAVT) at 210. The time out of this timer (AURAVTO) at 220 provokes the ventricular pace (VP) event at 230.

Figure 5:
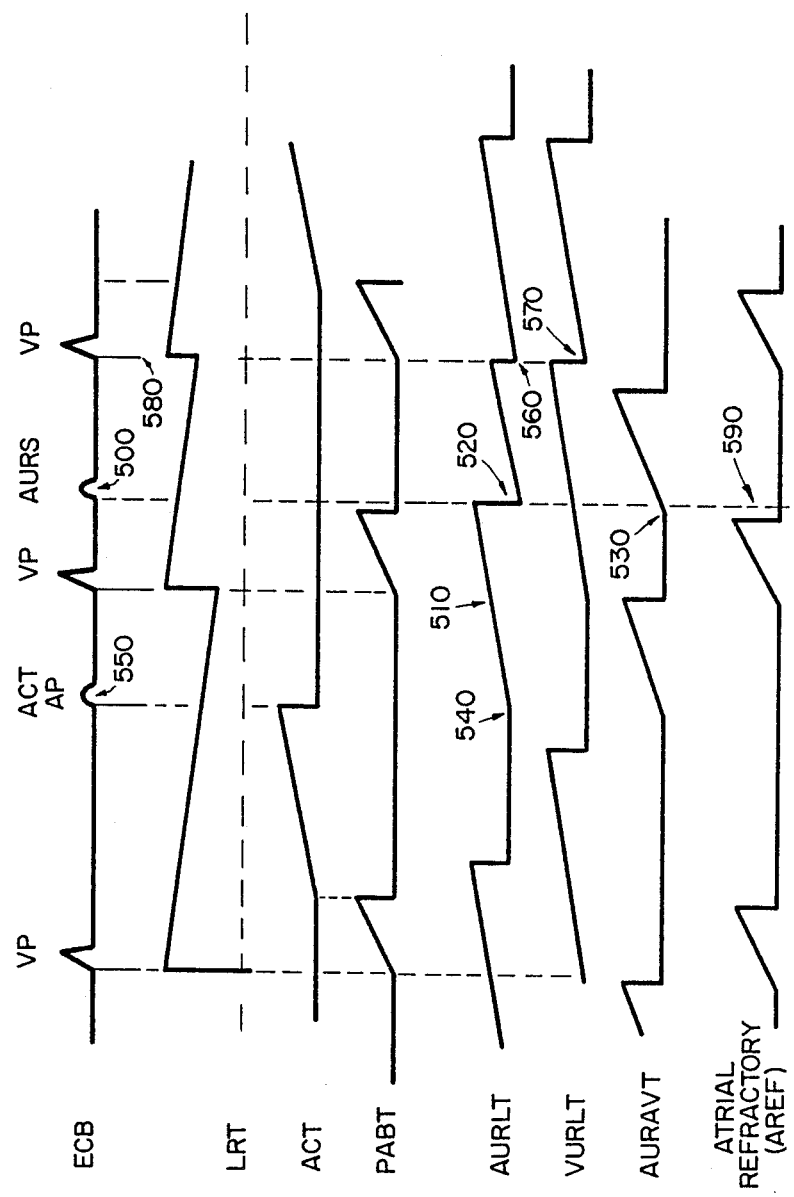
FIG. 5 is a timing diagram depicting the Wenkebach response of the pacer to ventricular sense events which occur during A-V extension occurring at high atrial rates.

An example of the AURAVT started by an atrial sense event and the time out of the atrial upper rate limit timer (AS∩AURLTO) is shown on FIG. 5 where the atrial sense event shown at 500 is detected outside of the atrial absolute refractory period 590, but during the atrial upper rate limit period 510. At this point the AURAVT is started at 530. During this rate limit period, atrial pacing is prohibited. At the conclusion of the ventricular upper rate limit period (VURLTO) shown at 570, a ventricular pace is delivered at 580.

Figure 9:
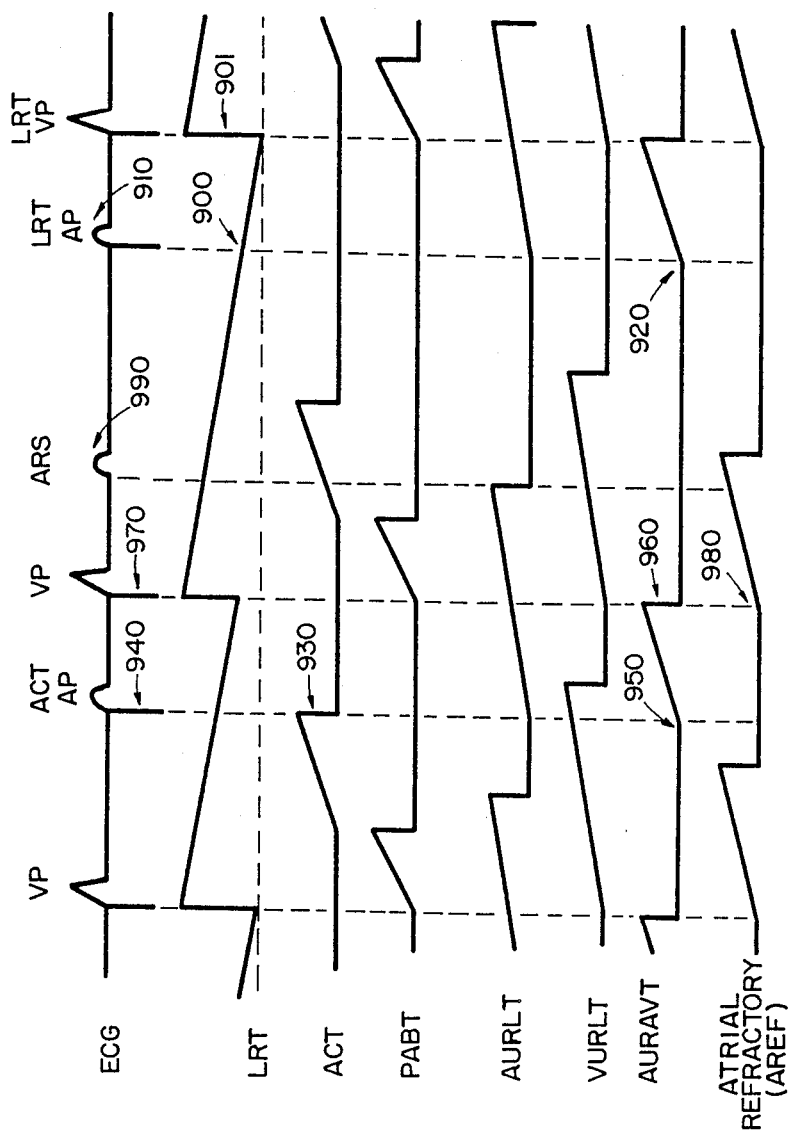
FIG. 9 is a timing diagram depicting the operation of the pacer to prevent atrial competition.

An example of the AURAVT started by the time out of the lower rate timer (LRTVATO) is shown at FIG. 9 where atrial pace event 910 is provoked by the LRTVATO shown at 900, which in turn starts the AURAVT at 920.

Note that ACTTO and LRTVATO may both result in atrial pace and that (AS∩AURLTO) and AS are essentially atrial sensing events. In many instances, this VP event sequence (Expression 5) will be synchronous with the VP event set forth in Expression 3. However, the LRT timer is not reset by atrial sense events while the AURAVTO timer is The functional result of this disparity is set forth in connection with FIG. 3.

Anti-Atrial Competition

At this point, the astute reader will wonder what action the pacer will take if the sinus rate and activity rate conflict. The mystery is revealed in FIG. 9 where AP event 940 has been provoked by ACTTO at 930 which initiates AURAV at 950. After one A-V delay, AURAVTO at 960 generates a VP at 970. This ventricular pace event (VP 970) starts an atrial refractory period at 980. The atrial sense event 990 occurs during the relative refractory period, but just outside the atrial upper rate limit period (AUR) and is ignored by the pacer which paces the atrium at the LRTVATO shown at 900 and previously discussed. Therefore, any P-wave detected in the post-ventricular portion of the atrial refractory period will in effect disable the activity based rate for that one pacing cycle forcing a lower rate escape and thus permitting resynchronization with the sinus rhythm.

C. Ventricular Sense Events

Several consequences of a ventricular sense event, or the lack thereof, have already been described. The alert reader will recall that on FIG. 6, a VS event 620 within the first 110 ms of the A-V delay period results in a VP event 600, as described in connection with the ventricular safety pace.

In a similar fashion, several of the Boolean expressions have assumed that a ventricular sense event has not occurred.

In the conventional DDD pacer, a ventricular sense during the V-A time interval of the pacer resynchronizes the pacer by resetting and restarting the lower rate timer. This is also true for the present pacer. An example of this is shown on FIG. 4 where the premature ventricular contraction (PVC) 400 resets and restarts the lower rate timer (LRT) at 410. This VS event also resets the activity timer (ACT) at 420, restarts the PABT at 430 and resets and restarts both the AURLT and VURLT at 440 and 450, respectively.

Figure 3:
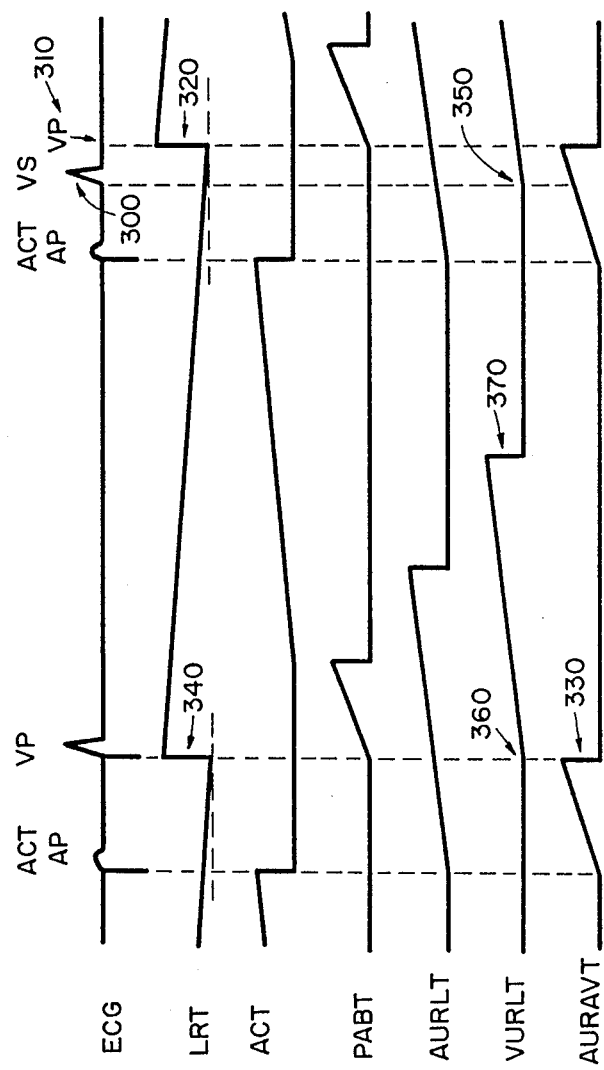
FIG. 3 is a timing diagram depicting the scheduled ventricular pace timing which shows that the A-V period is not truncated by a ventricular sense event.

In the traditional DDD pacer, a ventricular sense during the A-V time interval of the pacer restarts the V-A timer. This is not true for the present pacer. An example of this is shown in FIG. 3 where VS event 300 inhibits the otherwise scheduled VP at 310. Note, however, that the LRT and AURAVT are neither reset or restarted. This feature helps prevent rate acceleration due to short A-V conduction times.

D. Atrial Sense Events

As in the traditional DDD pacer, the detection of atrial activity starts the A-V delay period of the pacer. An example of this has been described in connection with FIG. 2 where AS event 200 starts the AURAVT at 210. When this timer times out (AURAVTO 220), a ventricular pace occurs at 230.

Turning to FIG. 5, when the atrial rate is high, the atrial sense event (AS 500) may occur during the atrial rate limit period (510) starting the AURAVT at 530. In this instance which has already been described, the ventricular pace 580 is delayed until the end of the ventricular upper rate limit period (570), giving rise to a Wenckebach event.

The preceding section described events which give rise to pace events and described what effect sense events have on the delivery of pacing stimuli.

The next section describes the logic governing each of the various timers which make up the pacer.

LRT

The lower rate timer is the basic timer which governs the pacer's lower rate behavior. When the physician programs the base pacing rate and A-V delay period for the patient, the pacer's V-A and A-V delay periods are established. And as described in connection with the first hypothetical example, the pacer issues pacing stimuli at the programmed V-V and A-V periods.

Therefore, the lower rate timer (LRT), in general, sets the V-A, V-V and the A-V escape intervals of the pacer. This timer may be reset and restarted by five events. These are: LRTAVTO; AURAVTO; PVC; (LRTVATO∩VS); VSPAVTO.

Each of these five events will cause this timer to reset to its nominal programmed value and to restart its timer function. These events will be described in the following order: LRTAVTO, AURAVTO, VSPAVTO, PVC and (LRTVATO∩VS).

The first event is the time out of the lower rate A-V delay timer function (LRTAVTO) which is shown on FIG. 9. The lower rate timer (LRT) reaches the conclusion of the lower rate timer A-V delay time at 901 which results in resetting the LRT timer and restarting it as shown in the FIG. at 901.

The second event is the time out of the atrial upper rate A-V delay timer (AURAVTO) which is shown throughout the drawing. Turning to FIG. 3, the time out of the AURAVT shown at 330 resets and restarts the LRT at 340.

The third event is the ventricular safety pace A-V time out which is shown on FIG. 6. The ventricular sense event shown at 620 occurs during the first 110 ms after the activity atrial pace 610. This AP event starts a VSPAVT which times out and generates the ventricular pace event 600 and restarts the LRT at 630.

The fourth event is a PVC which is the second of two consecutive ventricular events without an intervening atrial event. The PVC shown at 400 on FIG. 4 restarts and resets the LRT as shown at 410.

The fifth event is a ventricular sense event occurring during the V-A escape interval timed by the LRT. This is not shown on the drawing, but it is conventional in prior art DDD pacers such as the Funke machine described in U.S. Pat. No. 4,312,355.

PAB

The programmable activity blanking timer (PABT) is used to adjust the activity rate response characteristics of the pacer. The duration of the PAB interval is indirectly selected by the physician through his selection of a rate response and A-V interval characteristics for the pacer. This timer is reset to its nominal value and restarted by any one of four events. These events are: LRTAVTO; AURAVTO; PVC; and VSPAVTO.

The first event is the time out of the LRTAVT which is shown throughout the drawing. Turning to FIG. 2, for example, the LRTAVTO shown at 240 starts the PAB at 250. At the conclusion of the PAB time shown at 260, the ACT timer starts as shown at 270.

Figure 7:
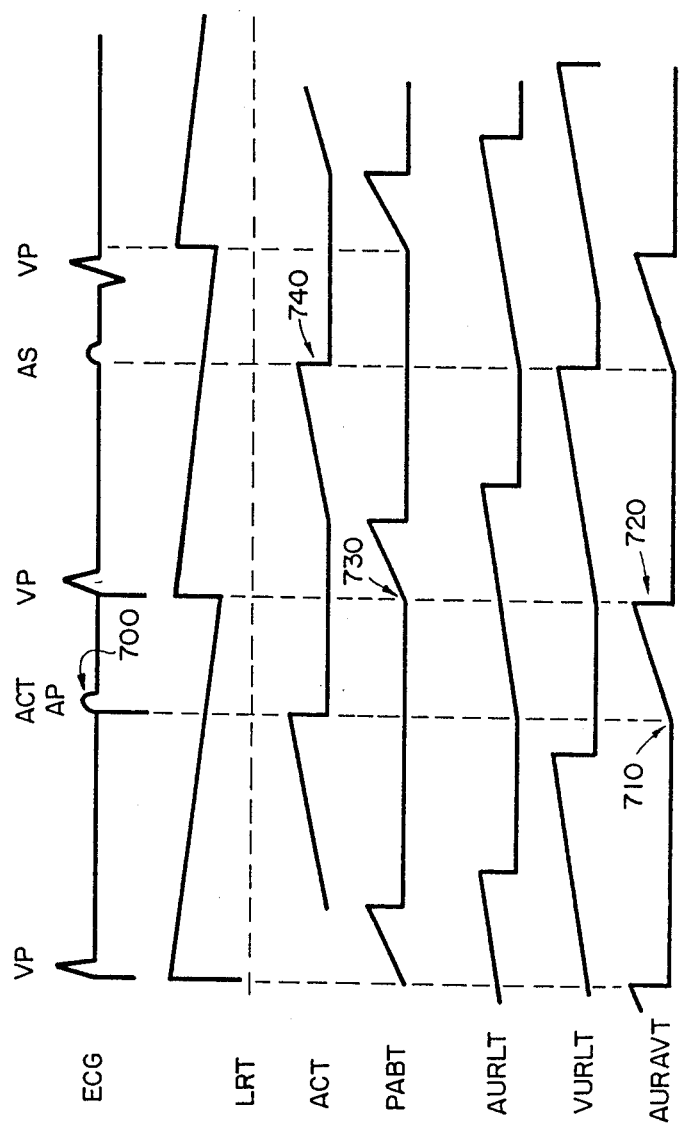
FIG. 7 is a timing diagram depicting intrinsic rates higher than the activity rate.

The second event is the AURAVTO which is shown at several places throughout the drawing including FIG. 7 where the AP event 700 starts the AURAVT at 710. At the conclusion of this time interval AURAVTO 720, the PAB starts as shown at 730.

Figure 4:
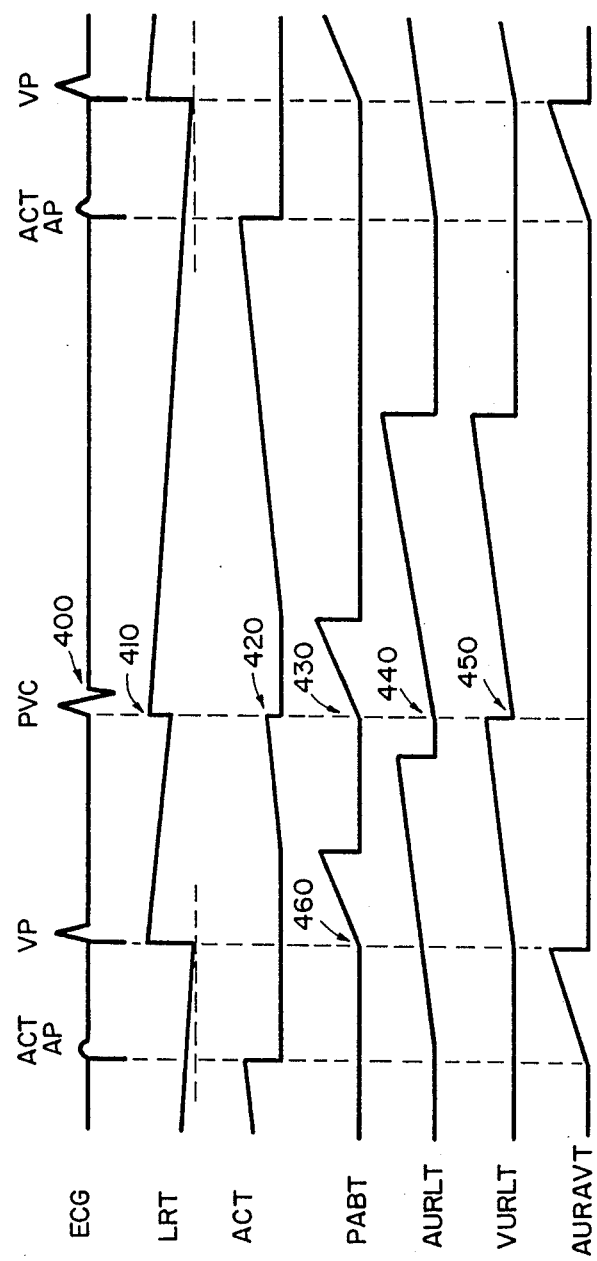
FIG. 4 is a timing diagram depicting the response of the pacer in response to a premature ventricular contraction.

The third event is the occurrence of a PVC, as shown in FIG. 4 where the PVC 400 starts the PAB at 430.

The fourth event is the time out of the safety pace escape timer. Note that the PAB starts at 640 on FIG. 6 at the time the VP event 600 occurs. This VP event occurs at the conclusion of the safety pace timer (not shown).

ACT

Figure 8:
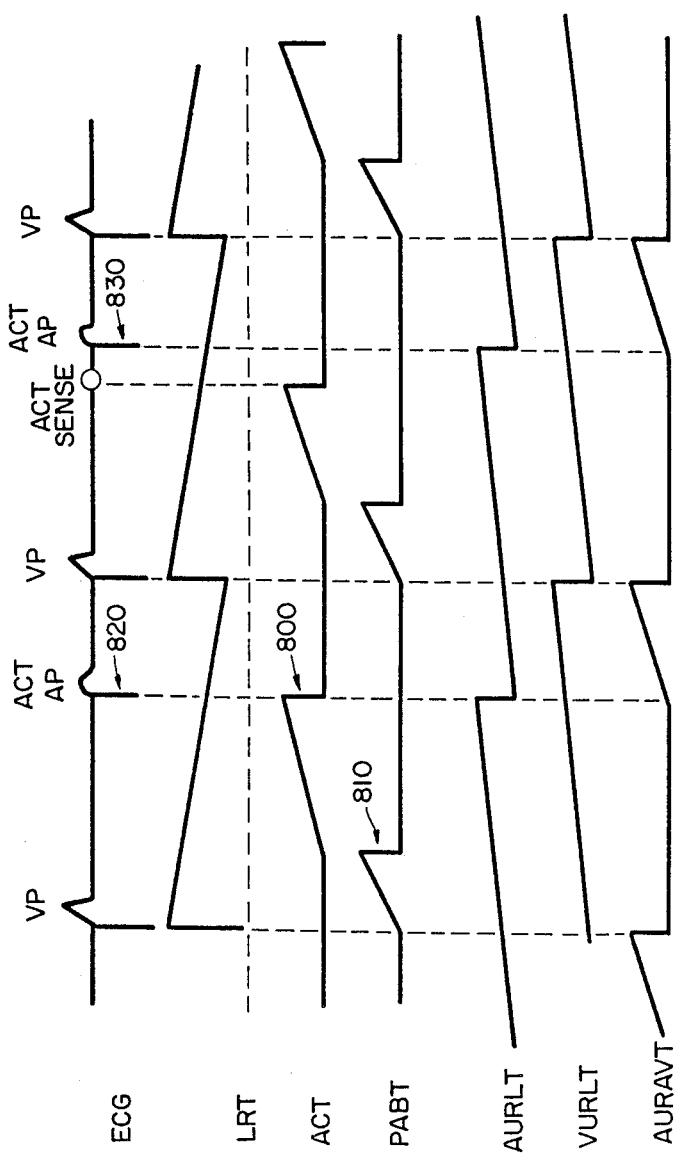
FIG. 8 is a timing diagram depicting an activity rate faster than the programmed upper rate.

The activity timer (ACT), in general, determines the end point or conclusion of the atrial escape interval as shown at 800 on FIG. 8. This timer is started by the conclusion of a programmable activity blanking interval (PAB) shown at 810. At the time out of this interval (ACTTO), the pacer generates an atrial pace event if the AURLT was timed out (ACTTO AURLTO) 830. This timer is reset as shown at 800 by either the activity timer time out (ACTTO) by detection of a PVC as shown at 420 on FIG. 4 or by an atrial sense or pace event as shown at 740 on FIG. 7.

AURAVT

The atrial upper rate timer is used to control pacer operation during periods of elevated atrial rate. This timer is started by an atrial event either sense or pace (AS or AP). During the interval timed by the AUR, pacing in the atrium is delayed. Atrial pace events scheduled to occur during this time period are delivered coincident with time out of the AUR timer 830. Unless an ASE occurs to cancel the scheduled event, this timer effectively limits the maximum rate of atrial stimulation.

The atrial upper rate A-V timer (AURAVT) is started by atrial sense events as shown at 210 on FIG. 2 as well as atrial pace events as shown at 280 on FIG. 2 which are caused by the time out of the activity timer.

At the time out of this A-V timer, a ventricular pacing event is scheduled to occur. Thus, this timer dictates the A-V interval of the pacemaker if an atrial sense event 200 or an activity atrial pace event occurs.

VURLT

The ventricular upper rate timer (VURLT) is used to control pacer operation during periods of elevated ventricular rate. This timer is started by a ventricular event either sense or pace (VS as shown at 350 on FIG. 3 or VP as shown at 360 on FIG. 3) and is reset by its own time out as shown at 370 on FIG. 3. During the interval timed out by the ventricular upper rate timer (VURLT), pacing in the ventricle is delayed. Ventricular pace events scheduled to occur during this time period are delivered coincident with the time out of the ventricular upper rate timer 580. Consequently, this timer effectively limits the maximum rate of ventricular stimulation unless a ventricular safety pace occurs.

AURLT

The atrial upper rate limit timer prevents pacing in the atrium during its timing period to prevent atrial stimulation at too high a rate.

This timer is started by atrial events either sense or pace or PVC's 440 or Wenckebach ventricular events 560. An example of atrial pace events are shown on FIG. 1 where lower rate escape AP 192 starts AURLT at 193. Note also the activity based AP 150 also starts the AURLT at 151. An example of atrial sense events is found on FIG. 2 where AS 200 starts AURLT at 290.

This timer may also be started by a sensed PVC as shown by 440 on FIG. 4 which results from the detector of PVC 400.

This timer will be reset and started by any V event that occurs when the A-V delay is extended, as for example during pacemaker Wenkebach. This is shown on FIG. 5. The AS event 500 occurs during the AURL period which started at 540 with the AP event 550. The occurrence of AS 500 initiates the AURAV at 530 and a ventricular pace event is then delivered at the VURLTO at 570. This means that the observed A-V delay is extended. This A-V extension operation is sometimes called pseudo-Wenkebach or pacer Wenkebach.

As shown in the figure, the AURLT is reset and restarted at 560 upon the time out of AURAVT at 570 when the A-V delay is extended.

In conjunction with the above written specification and drawings, we claim:

1. A cardiac pacemaker for implantation in a patient, said pacemaker comprising:
   ventricular output means for generating ventricular pacing stimuli;
   atrial output means for generating atrial pacing stimuli;
   atrial sensing means for sensing natural heart activity in the atrium;
   first timer means responsively coupled to said atrial sensing means and said ventricular output means for determining a first A-V interval following sensing of natural heart activity in the atrium and for triggering generation of a ventricular pacing stimulus by said ventricular output means at the expiration of said first A-V interval;
   second timer means responsively coupled to said atrial and ventricular output means for determining a V-A interval following generation of a pacing stimulus by said ventricular output means and for triggering generation of a pacing stimulus by said atrial output means at the expiration of said V-A interval;
   sensor means responsive to the physical activity of the patient in which said pacemaker is implanted for regulating the duration of said V-A interval;
   third timer means for determining an atrial refractory period following generation of a ventricular stimulus by said ventricular output means and for preventing initiation of said first A-V interval by said first timer means in response to the sensing of natural heart activity in the atrium during said atrial refractory period; and
   means for delaying generation of an atrial pacing stimulus by said atrial output means beyond the expiration of said V-A interval in response to the sensing of natural heart activity in the atrium during said atrial refractory period.

2. A cardiac pacemaker according to claim 1 further comprising means for triggering generation of a ventricular pacing pulse at the expiration of a second A-V interval following the generation of an atrial pacing pulse by said artial output means which was delayed by said delaying means.

3. A cardiac pacemaker according to claim 2 wherein said second A-V interval is the same as said first A-V interval.

* * * * *